United States Patent [19]
Nygaard et al.

[11] Patent Number: 6,063,965
[45] Date of Patent: May 16, 2000

[54] PRODUCTION OF DIETHANOLAMINE

[75] Inventors: Dennis M. Nygaard, Groves; Ralph M. Diguilio, Round Rock, both of Tex.

[73] Assignee: Huntsman Petrochemical Corporation, Austin, Tex.

[21] Appl. No.: 09/149,322

[22] Filed: Sep. 8, 1998

Related U.S. Application Data

[60] Provisional application No. 60/058,106, Sep. 5, 1997.

[51] Int. Cl.⁷ .................................................. C07C 213/00
[52] U.S. Cl. .............................................................. 564/477
[58] Field of Search ............................................... 564/477

[56] References Cited

FOREIGN PATENT DOCUMENTS 1529193  10/1978  United Kingdom .

OTHER PUBLICATIONS

McMillan, Thomas I., "Ethylene Oxide Derivatives" SRI International Report No. 193, Private Report by the Process Economics Program, Jan. 1991.

*Primary Examiner*—Samuel Barts
*Attorney, Agent, or Firm*—O'Keefe, Egan & Peterman

[57] ABSTRACT

This invention concerns a process for preparation of alkanolamines such as diethanolamine (DEA) from ammonia and an alkylene oxide such as ethylene oxide. The yield of DEA may be increased by adding monoethanolamine (MEA) to the second feed in a split feed reactor scheme. The process can be conducted as a multistep process, such as by reacting a portion of the ethylene oxide followed by addition of a second charge of ethylene oxide after complete reaction of the first charge of ethylene oxide.

20 Claims, 1 Drawing Sheet

PRODUCTION OF DIETHANOLAMINE

This application claim the benefit of provisional application No. 60/058,106 filed Sep. 5, 1997.

BACKGROUND OF INVENTION

This invention concerns production of alkanolamines, especially diethanolamine in higher yields.

The production of alkanolamines is well known. Alkanolamines such as monoethanolamine ("MEA"), diethanolamine ("DEA") and triethanolamine ("TEA") are commonly made by reacting aqueous ammonia and an alkylene oxide such as ethylene oxide under suitable conditions to form the alkanolamine. This reaction generally produces a variety of alkanolamines. For example, reaction of aqueous ammonia and ethylene oxide typically produces a mixture of MEA, DEA, and TEA. It is well known that the relative amounts of MEA, DEA, and TEA produced are a function of the ammonia/ethylene oxide ratio. While it is known that the ammonia/ethylene oxide ratio can be adjusted to obtain 80–90 percent MEA or 80–90 percent TEA, the maximum amount of DEA in the mixture previously achievable is about 35 percent. Owing to its significant commercial utility, a process which increases the yield of DEA would be highly desirable.

SUMMARY OF INVENTION

In one broad respect, this invention is a process for the production of dialkanolamine, comprising: adding a stoichiometric deficiency of alkylene oxide to a first mixture of ammonia and water under conditions effective to form a second mixture comprising water, ammonia, monoalkanolamine, dialkanolamine and trialkanolamine for a time sufficient to react substantially all the alkylene oxide; adding monoalkanolamine and additional alkylene oxide to the second mixture under conditions effective to react substantially all the additional alkylene oxide thereby forming a third mixture comprising monoalkanolamine, dialkanolamine and trialkanolamine.

As used herein, "stoichiometric deficiency" means an amount of alkylene oxide that is needed to quantitatively form a given dialkanol amine. For example, if EO and ammonia are to be reacted to form DEA, while a stoichiometric amount of EO would be two moles per mole of ammonia, a stoichiometric deficiency would be less than two moles of EO.

In another broad respect, this invention is a process for the production of diethanolamine, comprising adding ethylene oxide to aqueous ammonia under conditions effective such that substantially all the ethylene oxide has reacted to form a second mixture comprising water, ammonia, monoethanolamine, diethanolamine, and triethanolamine, wherein a molar excess of ammonia is employed relative to ethylene oxide; and adding additional ethylene oxide and monoethanolamine to the second mixture under conditions effective to react substantially all the additional ethylene oxide to form a third mixture comprising monoethanolamine, diethanolamine and triethanolamine.

In another broad respect, this invention is an apparatus useful for the production of alkanolamines comprising a first reactor, a second reactor that receives effluent from the first reactor, a separation column for removing monoalkanolamines from a mixture of monalkanolamine, dialkanolaminc, and trialkanolamine, and a line directly or indirectly connecting the column to convey separated monoalkanolamine to the second reactor.

This invention has a number of advantages. The process of this invention produces surprisingly high yields of DEA. More surprisingly, this result is achieved without increasing the amount of TEA generated. Indeed, TEA manufacture is reduced through practice of this invention relative to a process where no MEA recycle is performed as well as relative to a process wherein MEA is recycled to the first reactor rather than the second reactor as in this invention. Reduction in TEA amounts is highly desirable since this co-product cannot be recycled for production of DEA.

As indicated above, this invention finds utility in the manufacture of alkanolamines, articularly diethanolamine.

DETAILED DESCRIPTION OF THE INVENTION

Figure 1:
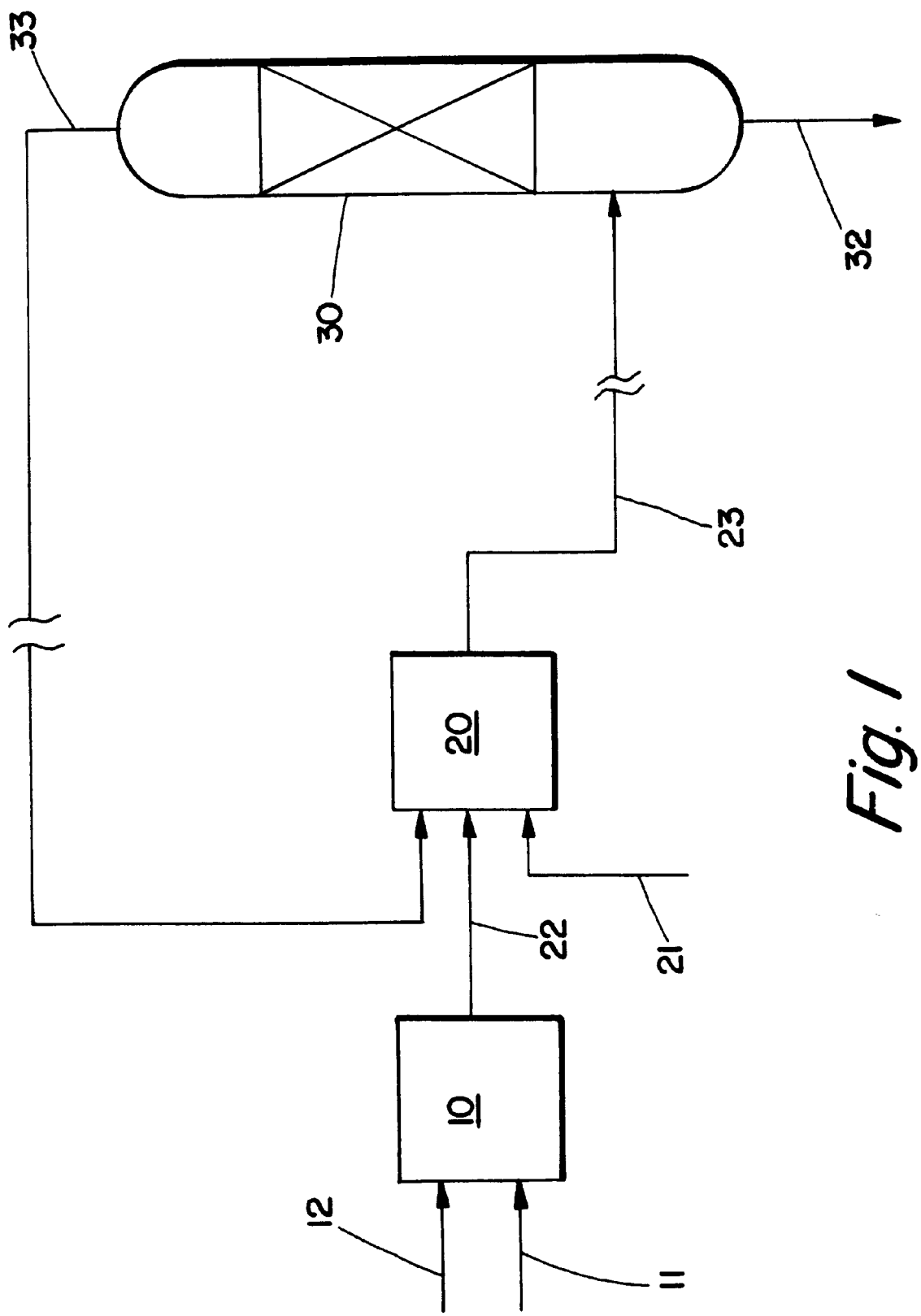
FIG. 1 illustrates a process scheme and apparatus of this invention.

The process of this invention, and apparatus thereof may be practiced using conventional reactors to carry out the addition of alkylene oxide such as EO, and ammonia or monoalkanolamine such MEA, such that alkanolamines are manufactured. While batch and other reactors are useful, it is often preferred to employ tubular reactors such as a plug flow tubular reactors for continuous reaction. Each reactor may be composed of up to several hundred tubes, such as a group of 20 foot, one-half inch internal diameter tubes. Tubes of varying length and diameter may be used. Such reactors are typically equipped with suitable ports for introduction of starting materials. The reactors can be connected in series. A process may employ two or more reactors, with two or three reactors being preferred in the practice of this invention. In the production of alkanolamines from alkylene oxides and ammonia, the reactors may be packed with catalyst; however, catalysts are not required and commercial operations typically do not use catalysts. Effluent from a given reactor may be cooled prior to introduction into the succeeding reactor.

In the practice of this invention, alkylene oxide, such as EO, and ammonia are fed to the first reactor. The ammonia/alkylene oxide ratio is commonly adjusted to modify the product distribution. A molar excess of ammonia is frequently maintained to promote MEA production. In the process of this invention, on the other hand, dialkanolamine such as DEA production is emphasized. While a weight of about 3:1 ratio of ammonia:alkylene oxide may be conveniently employed, this ratio may vary depending on a variety of factors such as reactor design, extent of split feed, and so on. In general, the weight ratio may range from about 1:1 to about 10:1. It should be appreciated that this weight ratio represents that obtained which is by the sum total amount of alkylene oxide added if a split feed is employed.

The temperature at which the reaction may occur may vary widely. In general, the temperature of the first and second reaction mixtures may be varied, independently, in the range from about 25° C. to about 250° C. More typically, the temperature is maintained at a temperature in the range from about 38° C. (100° F.) to about 205° C. (400° F.), more preferably above about 65° C. (150° F.).

Ammonia is usually added as an aqueous solution to the reactor. While any concentration which produces alkanolamines is acceptable, the ammonia solution usually has a concentration in the range from about 20% to about 40% by weight and more typically is from about 30% to about 40%.

In the practice of this invention, the oxide may be split such that it is introduced into both the first and second reactors (and additional reactors if used). If 100 parts oxide are to be added, the amount added to the first reactor may vary from about 1 to about 99 parts (i.e., about 1% to about 99%), with an amount greater than 50% being typically used. The amount added to the first reactor may be, for example, about 60 to about 80 percent by weight. Such a split feed scheme is described, for example in Chemical Abstracts 96(7):51806 g, which is an abstract of Brazil Patent 8003904-A (1981). In one embodiment of this invention, the ammonia/alkylene oxide ratio in the first reactor is from about 3:1 to about 5:1 and typically about 3.5:1, with the range in the second reactor being about 3:1 to about 7:1 and typically about 5:1.

The process of this invention may advantageously produce 35% or more dialkanolamine, preferably 40% or more, with no more than about 30% TEA being produced, preferably less about 25% trialkanolamine.

The process of this invention may be practiced batchwise, continuously, or intermittently.

After reaction of substantially all the oxide, effluent from a given reactor may be separated and purified. Generally, effluent from the reactors flows to one or more distillation columns where water is first distilled off, then monoalkanolamine, dialkanolamine, and trialkanolamine are separated from one another. Such distillation techniques are well known.

The practice of this invention may be further appreciated with reference to the appended FIG. 1. In FIG. 1, oxide such as an ammonia enter first reactor 10 via lines 11 and 12 to form a first mixture. In this scheme, less than 100% of the alkylene oxide to be added is added to reactor 10. After maintaining the reaction at a given temperature until the reaction is substantially complete, a second mixture is produced which is conveyed to second reactor 20 via conduit 22. Additional oxide may be introduced via line 21. Upon reaction, a final mixture is produced which contains mono-, di-, and tri-alkanolamines. The final mixture is transported to column 30 through conduit 23. After removing water, monoalkanolamine take off overhead is recycled to second reactor 20 via line 33. It should be appreciated that line 33 may include a hold tank, not shown, to collect monoalkanolamine as desired, which can be dispensed to second reactor 20 on demand. Dialkanolamine and tri-alkonolamine may be removed via line 32 and sent on for further processing. Alternatively, column 30 may be used to further distill off the dialkanolamine as when a suitable located valve is closed to prevent the dialkanolamine from entering second reactor 20.

This invention may optionally be practiced whereby the monoalkanolamine is added to the second mixture in an amount effective to increase the percentage of dialkanolamine in the third mixture relative to the percentage of dialkanolamine obtained from an identical process with the proviso that the identical process does not add monoalkanolamine to the second mixture. In the practice of this invention, the monoalkanolamine added to the second mixture may be obtained from the third mixture. This process may be conducted wherein the first mixture and second mixture are each maintained at a reaction temperature in the range from about 50° C. to about 250° C. The first and second mixtures may each maintained at a pressure in the range from about 50 psi to about 2000 psi. The mixture of ammonia and water may contain ammonia in an amount of at least 15 percent by weight. A catalyst is not required in the practice of this invention, but may optionally be employed.

The alkylene oxides which may be used in the practice of this invention may vary widely, and typically contain 2 to 20 carbons. Non-limiting examples of such alkylene oxides include ethylene oxide, propylene oxide, butylene oxide, hexylene oxide, and so forth. While a mixture of alkylene oxides may be added to a given reactor, it is preferred that a single alkylene oxide is added to each reactor. Ethylene oxide is the most preferred alkylene oxide used in the practice of this invention. The monoalkanolamine added to the second reactor preferably is derived from the same alkylene oxide being added to the second reactor, although a different material may be used if a dialkanolamine is desired having two different alkanol substituents, such as ethanol propanolamine. The preferred products of this invention are derived from ethylene oxide, with the production of diethanolamine being most preferred.

The following examples are illustrative of this invention and are not intended to be limit the scope of the invention or claims hereto. Unless otherwise denoted all percentages are by weight. In the examples "gpm" means gallons per minute. In the examples, the process was simulated using kinetic data for production of ethanolamines with Aspen Plus™ software.

EXAMPLE 1

65 gpm ethylene oxide (EO) (60% EO to reactor 1, 40% to reactor 2) and, 200 gallons gpm of 36.0 weight % ammonia are fed to the first of three reactors in series. The second EO charge is fed to the second reactor in series.

With 5000 pounds per hour of MEA being added to reactor 1, the product distribution is:

24.3% MEA
40.5% DEA
35.2% TEA

With 5000 pounds per hour of MEA being added to reactor 2, the product distribution is:

29.9% MEA
41.0% DEA
29.2% TEA

This examples illustrates achieving an increase in DEA selectivity with less TEA production. The process is composed of two elements. First, the total EO feed is split to the reactor system in two feeds. One of these feeds (about 60% of the total for example) is fed to the first reactor in the train. The second feed goes into the second reactor of the train. Secondly, MEA is recycled to the second train in the series. This provides for an effectively higher EO:NH3 mole ratio in the first reactor (improving selectivity to the MEA in the first reactor) which subsequently improves selectivity to the DEA in the second reactor where the MEA and additional EO are combined. The net result is higher DEA without additional TEA.

EXAMPLE 2

65 gpm ethylene oxide (EO) (60% EO to reactor 1, 40% to reactor 2), 200 gallons gpm (36.0 weight % ammonia) are fed to the first of three reactors in series. The second EO charge is fed to the second reactor in series.

With 6000 pounds per hour of MEA being added to reactor 1, the product distribution is:

22.1% MEA
41.7% DEA
36.3% TEA

With 6000 pounds per hour of MEA being added to reactor 2, the product distribution is:

28.8% MEA 42.1% DEA 29.1% TEA

This examples illustrates achieving an increase in DEA selectivity with less TEA production. It has been found that recycling MEA at 7 gpm to the second reactor in a three reactor train increases DEA production by 10% with no increase in TEA production.

EXAMPLE 3

Cases were studied as follows: (1) all EO fed to the first reactor (with and without MEA recycle fed to the first and second reactors) and (2) all EO feed split 70/30 between the first and second reactors (with and without MEA recycle fed to the first and second reactors).

The case in which MEA recycle is input to the second reactor and all the EO is fed to the first reactor is not useful as most of the EO is reacted by the time the recycle MEA enters the reactor train. Table 1–3 below give the results for the other three cases.

The results show how little difference in product distribution between the cases where all EO and MEA recycle are input to the first reactor and that in which EO is split between reactors and MEA recycle is input to the first reactor. The case in which the EO feed is split (70/30) and the MEA recycle is input into the second reactor allows for adjusting the MEA/DEA production without changing the TEA production. It may be possible to further reduce the amount of TEA produced by adjusting the ratio of ammonia to EO.

TABLE 1: Comparative experiments not representative of the invention. Gross product distributions resulting from 3:1 ammonia:EO molar ratio at 34.25 weight percent ammonia in the aqueous reactor feed at various level of MEA recycle. All EO and MEA recycle input to first reactor.

| Percent of crude MEA recycled | MEA (weight %) | DEA (weight %) | TEA (weight %) |
| --- | --- | --- | --- |
| 0 | 36.6 | 35.0 | 27.5 |
| 32.2 | 26.8 | 39.6 | 32.7 |
| 59.6 | 17.5 | 44.8 | 36.7 |
| 81.8 | 8.8 | 50.5 | 39.8 |

TABLE 2: Comparative experiments not representative of the invention. Gross product distributions resulting from 3:1 ammonia:EO molar ratio at 34.25 weight percent ammonia in the aqueous reactor feed at various level of MEA recycle. EO split 70/30 split feed, with 30% to reactor 1 and 70% to reactor 2. MEA recycle input to first reactor.

| Percent of crude MEA recycled | MEA (weight %) | DEA (weight %) | TEA (weight %) |
| --- | --- | --- | --- |
| 0 | 37.3 | 35.1 | 26.7 |
| 31.4 | 27.8 | 39.8 | 31.6 |
| 58.1 | 18.6 | 45.0 | 35.4 |
| 79.8 | 9.9 | 50.7 | 38.4 |

TABLE 3: Gross product distributions resulting from 3:1 ammonia:EO molar ratio at 34.25 weight percent ammonia in the aqueous reactor feed at various level of MEA recycle. EO split 70/30 split feed, with 30% to reactor 1 and 70% to reactor 2. MEA recycle input to second reactor.

| Percent of crude MEA recycled | MEA (weight %) | DEA (weight %) | TEA (weight %) |
| --- | --- | --- | --- |
| 0 | 37.3 | 35.1 | 26.7 |
| 27.0 | 33.2 | 39.5 | 26.4 |
| 45.9 | 29.8 | 43.4 | 26.0 |
| 58.6 | 26.8 | 46.8 | 25.6 |

It should be noted that in Table 1, the production of TEA increases undesirably with increasing recycle of MEA to reactor 1. In Table 2 it is seen that the split feed promotes a reduction in TEA manufacture relative to the data in Table 1; however, the TEA production levels remain undesirably high. Surprisingly, Table 3 shows that by recycling the MEA back to reactor 2, TEA production decreases significantly as compared to both the comparative experiments in Table 1 (no recycle) and Table 2 (recycle to reactor 1). This result is unexpected and surprising.

EXAMPLES 4 and 5

Table 4 shows comparative experiments constituting additional runs at various temperatures. Table 5 illustrates examples of this invention.

TABLE 4

Comparative Experiments
(60 gallons per minute EO, 200 gallons per minute ammonia (34.5 weight percent ammonia) to Reactor 1 and no MEA recycle)

| Reaction Temp | MEA Pound/day (in 1000's) | DEA Pound/day (in 1000's) | TEA Pound/day (in 1000's) | Total Pound/day (in 1000's) | MEA weight % | DEA weight % | TEA weight % |
| --- | --- | --- | --- | --- | --- | --- | --- |
| 200 | 286.9 | 273.4 | 208.7 | 769.0 | 37.3 | 35.6 | 27.1 |
| 220 | 284.0 | 273.0 | 211.4 | 786.4 | 37.0 | 35.5 | 27.5 |
| 240 | 280.7 | 272.2 | 214.8 | 767.7 | 36.6 | 35.5 | 28.0 |
| 260 | 276.4 | 270.3 | 220.1 | 766.8 | 36.0 | 35.3 | 28.7 |
| 280 | 267.2 | 263.6 | 234.0 | 764.8 | 34.9 | 34.5 | 30.6 |

TABLE 5

(60 gallons per minute EO, 200 gallons per minute ammonia (36 weight percent ammonia) to Reactor 1, with 5000 pound/hour MEA recycle to reactor 2)

| Reaction Temp | MEA Pound/day (in 1000's) | DEA Pound/day (in 1000's) | TEA Pound/day (in 1000's) | Total Pound/day (in 1000's) | MEA weight % | DEA weight % | TEA weight % |
|---|---|---|---|---|---|---|---|
| 240 | 197.9 | 330 | 286.3 | 814.2 | 24.3 | 40.5 | 35.2 |
| 240 | 246.2 | 337.9 | 24.4 | 824.5 | 29.9 | 41.0 | 29.2 |
| 240 | 179.4 | 338.5 | 293.4 | 811.3 | 22.1 | 41.7 | 36.2 |
| 240 | 237.4 | 346.4 | 239.6 | 823.4 | 28.8 | 42.1 | 29.1 |

What is claimed is:

1. A process for the production of dialkanolamine, comprising:

adding a stoichiometric deficiency of alkylene oxide to a first mixture of ammonia and water under conditions effective to form a second mixture comprising water, ammonia, monoalkanolamine, dialkanolamine and trialkanolamine for a time sufficient to react substantially all the alkylene oxide;

adding monoalkanolamine and additional alkylene oxide to the second mixture under conditions effective to react substantially all the additional alkylene oxide thereby forming a third mixture comprising monoalkanolamine, dialkanolamine and trialkanolamine.

2. The process according to claim 1 wherein the monoalkanolamine is added to the second mixture in an amount effective to increase the percentage of dialkanolamine in the third mixture relative to the percentage of dialkanolamine obtained from an identical process with the proviso that the identical process does not add monoalkanolamine to the second mixture.

3. The process according to claim 1 wherein the monoalkanolamine added to the second mixture is obtained from the third mixture.

4. The process according to claim 1 wherein the first mixture and second mixture are each maintained at a reaction temperature in the range from about 50° C. to about 250° C.

5. The process according to claim 1 wherein the first and second mixtures are each maintained at a pressure in the range from about 50 psi to about 2000 psi.

6. The process according to claim 1 wherein the mixture of ammonia and water contains ammonia in an amount of at least 15 percent by weight.

7. The process according to claim 1 wherein the molar ratio of ammonia to the total amount of alkylene oxide added to the first mixture is greater than 3:1.

8. The process according to claim 7 wherein the molar ratio of ammonia to the total amount of alkylene oxide added to the first mixture is from about 3:0.5 to about 3:0.7.

9. The process according to claim 1 wherein the molar ratio of ammonia in the first mixture to the total amount of alkylene oxide added to the first mixture and the third mixture is about 3:1.

10. The process of claim 1, wherein the alkylene oxide has from 2 to 20 carbons.

11. The process of claim 1, wherein the alkylene oxide is ethylene oxides.

12. A process for the production of diethanolamine, comprising:

adding ethylene oxide to aqueous ammonia under conditions effective such that substantially all the ethylene oxide has reacted to form a second mixture comprising water, ammonia, monoethanolamine, diethanolamine, and triethanolamine, wherein a molar excess of ammonia is employed relative to ethylene oxide; and adding additional ethylene oxide and monoethanolamine to the second mixture under conditions effective to react substantially all the additional ethylene oxide to form a third mixture comprising monoethanolamine, diethanolamine and triethanolamine.

13. The process according to claim 12 wherein the monoalkanolamine is added to the second mixture in an amount effective to increase the percentage of dialkanolamine in the third mixture relative to the percentage of dialkanolamine obtained from an identical process with the proviso that the identical process does not add monoalkanolamine to the second mixture.

14. The process according to claim 12 wherein the monoalkanolamine added to the second mixture is obtained from the third mixture.

15. The process according to claim 12 wherein the first mixture and second mixture are each maintained at a reaction temperature in the range from about 50° C. to about 250° C.

16. The process according to claim 12 wherein the first and second mixtures are each maintained at a pressure in the range from about 50 psi to about 2000 psi.

17. The process according to claim 12 wherein the mixture of ammonia and water contains ammonia in an amount of at least 15 percent by weight.

18. The process according to claim 12 wherein the molar ratio of ammonia to the total amount of alkylene oxide added to the first mixture is greater than 3:1.

19. The process according to claim 12 wherein the molar ratio of ammonia to the total amount of alkylene oxide added to the first mixture is from about 3:0.5 to about 3:0.7.

20. The process according to claim 12 wherein the molar ratio of ammonia in the first mixture to the total amount of alkylene oxide added to the first mixture and the third mixture is about 3:1.

* * * * *